United States Patent [19]

Rasmussen et al.

[11] 4,264,305
[45] Apr. 28, 1981

[54] INSTRUMENT AND METHOD FOR MAKING DENTAL IMPRESSIONS

[76] Inventors: Jack D. Rasmussen, 77 E. 7th St., Upland, Calif. 91786; Roy K. Fujitaki, 721 E. Mendocino St., Altadena, Calif. 91001

[21] Appl. No.: 50,780

[22] Filed: Jun. 21, 1979

Related U.S. Application Data

[63] Continuation-in-part of Ser. No. 776,304, Mar. 10, 1977, abandoned.

[51] Int. Cl.³ .............................................. A61C 5/04
[52] U.S. Cl. ..................................... 433/90; 433/214
[58] Field of Search .................. 222/4, 325, 326, 327; 433/89, 90, 80

[56] References Cited

U.S. PATENT DOCUMENTS

| | | | |
|---|---|---|---|
| Re. 15,527 | 1/1922 | Williams | 222/325 |
| 3,530,587 | 9/1970 | Anderson | 222/4 |
| 3,722,097 | 3/1973 | Colman | 433/36 |

*Primary Examiner*—Robert Peshock
*Attorney, Agent, or Firm*—Fraser and Bogucki

[57] ABSTRACT

A gun-like instrument for making dental impressions, comprising an outer air nozzle and an inner nozzle for impression material within the outer nozzle, the inner nozzle projecting beyond the tip of the outer nozzle so that any tendency of the impression material to plug the outer nozzle is eliminated. The air emanating from the outer nozzle first removes debris from the operative area, and then causes the impression material to impinge on the tooth in such a way as to form an accurate impression. The instrument includes a hand grip having a finger operable trigger forwardly thereof for discharging impression material from the inner nozzle, a valve for discharging air from the air nozzle, and thumb operable valve actuators on opposite sides of the instrument for opening the air valve. With this construction, the fingers can be used to control the discharge of impression material, while the thumb is used to control the discharge of air independently. Equipping the instrument with thumb operable valve actuators on opposite sides thereof renders the instrument usable by either a left-handed or a right-handed operator.

20 Claims, 8 Drawing Figures

INSTRUMENT AND METHOD FOR MAKING DENTAL IMPRESSIONS

This application is a continuation-in-part of our previously filed application for patent entitled "Instrument For Making Dental Impressions", filed Mar. 10, 1977, Ser. No. 776,304 and now abandoned.

BACKGROUND OF THE INVENTION

The present invention relates in general to an instrument for making dental impressions and, more particularly, to a gun-like instrument which first cleans the area in which an impression is to be made with compressed air, and which then applies the impression material thereto. Still more particularly, the present invention relates to a gun-like instrument similar in a general sense to that disclosed in U.S. Pat. No. 3,530,587, issued Sept. 29, 1970, to Robert Leo Anderson, reference to which is hereby made for further background.

Dentist's impression material is prepared by mixing base and catalyst materials just prior to the time at which an impression is to be taken. Depending upon a number of minor variables, such as temperature, the particular chemicals and the amount of catalyst used, a limited amount of time is available for taking the impression. Prior to this time, a dentist has usually completed preparation of the patient for taking the impression, which involves both cleaning the area and adequately exposing the tooth at or below the gum line, as necessary, for reception of the impression material. The groove defined between the tooth and gum in this region is usually referred to as the "sulcus". In addition, it is important that each other concave and convex surface on which the impression material is to be placed be dry, because the impression material does not otherwise adhere. The presence of seepage and the physical characteristics of the impression material tend to introduce voids, bubbles, and incompletely filled areas into the impression. The more intricate the concavities and convexities, the less likely it is that these critical regions will be adequately filled.

Consequently, when a casting is to be made it is often necessary for the dentist or technician to study the matter very carefully and to interpolate, extrapolate or actually "fake" the margin line and the contours needed for the final casting. If the edges and margins of the final casting do not precisely match the prepared area of the tooth at or below the gum line, the process of decay can quickly be renewed and the useful life of the filling can be substantially shortened.

Major difficulties arise with present extrusion type impression instruments, because the impression material is flowable under pressure, but has a rubbery and elastomeric characteristic even while setting. The impression material will take the shape of something against which it is pressed, but adequate and equal pressure should be exerted on all sides to insure conformance to complex shapes. Consequently, the sulcus around the gum line of a tooth being prepared for receiving a casting cannot be filled simply by pressing an adequate amount of material toward it. Other concavities and some convex portions also will create problems unless they are precisely defined by an initial layer or film of adherent impression material.

The characteristics of the impression material can be particularly troublesome when seepage of blood or saliva occurs, as very readily happens because of the circumstances under which the impression is taken. To obtain clear access to the sulcus and the margin line which the casting base is to follow, a packing material is often used to separate the gum from the tooth in this region. Seepage begins as soon as the packing material is taken out, or can be continuous if no packing is used. The impression material will not adhere to a wet surface but instead, slips to another region. This, together with the rubbery characteristic of the impression material, contributes further to the uncertainties in the location of margins and contours which require interpolation and extrapolation to attempt to define the proper shape. It will be borne in mind that an accurate impression must be taken as expeditiously as possible, for the benefit of both the patient and the dentist. To accomplish this a versatile instrument capable of being used in different ways to overcome different problems is highly desirable but has not heretofore been available.

SUMMARY OF THE INVENTION

A primary object of the invention is to provide an instrument for making dental impressions which includes an outer air nozzle and an inner nozzle for impression material within the outer nozzle. With this construction, after cleaning the area in which an impression is to be made with one or more air blasts, additional air blasts or a continuous air blast surrounding the impression material discharged by the inner nozzle may be used to cause the impression material to impinge on the tooth which is being worked on. Causing the impression material to impinge on the tooth in this manner results in a dense and accurate impression, which is an important feature.

It is important to note that the air impinging on the tooth removes debris, dries the tooth, and permits the application of elastomeric impression materials to the tooth. The impression material will not adhere if the tooth is not clean and dry. It is blown away and replaced with material which does adhere to a clean and dry tooth.

Another and important object related to the foregoing is to provide generally coaxial nozzles wherein the inner nozzle for the impression material projects beyond the tip of the outer air nozzle. With this construction, any possibility of plugging of the air nozzle by the impression material is eliminated, which is an important feature.

Impression instruments in accordance with the invention satisfy the various requirements imposed by this delicate work, by concurrently flowing a cylindrical shell of pressurized air about an interior extrudable column of impression material that is separately controllable. The pressurized air emanates from the nozzle with concentrated flow of sufficient volume and velocity to eject seepage at the target area and to thoroughly and substantially immediately dry the prepared target area. Impression material is fed along the center of the air flow sheath and is attenuated into a thin converging and protruding column. Using concurrent material feed and air flow, the tip of the protruding column separates at a certain distance from the nozzle tip, causing small globules of the impression material to be directed into the target region. Alternatively the protruding material may be deposited directly on a desired accessible area simply by contact. Concurrently or subsequently the air flow spreads the globules or deposited mass into an adherent thin film. Thus, with receiving surface area dry, and with a readily controlled and precisely directed supply of impression material, the dentist has excellent control. He can often readily observe the proper buildup of the adherent thin film upon the complex surfaces of the immediate target region, or where there is no visibility he can assure development of an adherent film by repeated applications of material. He can quickly move along the sulcus all about the periphery of the tooth and insure that all of the least accessible and most critical regions have been filled. In doing this he can apply material and air flow in various modes best suited to the specific conditions he encounters. When a larger mass of impression material is then overlaid in position on one or a number of teeth, and allowed to set into its cured elastomeric state, the result is an impression which requires substantially no interpolation or extrapolation.

The present invention may be summarized as including, and another important object is to provide an instrument for making dental impressions which includes: a gun having a hand grip and having a finger operable trigger forwardly of the hand grip for discharging impression material from the impression nozzle; valve means for discharging air from the air nozzle; and a thumb operable valve actuator for the valve means mounted on one side of the instrument adjacent the upper end of the trigger. With this construction, compressed air and impression material may be discharged selectively and/or simultaneously with one hand, using the fingers for the impression material and the thumb for the compressed air, which is an important feature.

Yet another important object is to provide a second thumb operable valve actuator for the air valve mounted on the opposite side of the gun from the first valve actuator mentioned, whereby the instrument may be readily operated by either a left-handed or a right handed operator.

The invention may be further summarized as including, and an additional object of the invention is to provide an instrument for making dental impressions which includes: a gun having a housing and a hand grip and having a cylinder terminating in a nozzle for discharging impression material; a plunger in the cylinder for expelling impression material through the nozzle; a rack in the housing and connected to the plunger; a pinion in the housing and meshed with the rack; a ratchet wheel in the housing and connected to the pinion; a trigger pivotally mounted on the gun adjacent and forwardly of the hand grip; a pawl pivotally mounted on the trigger and engageable with the ratchet wheel to rotate the ratchet wheel in a direction to advance the plunger; and a second pawl pivotally mounted on the housing and engageable with the rachet wheel to prevent rotation of the ratchet wheel in the opposite direction.

A further object is to provide an instrument of the foregoing nature wherein the housing includes a pivoted cover openable to provide access to the rack, the instrument including means responsive to opening of such cover for disengaging the second pawl from the ratchet wheel so that the plunger may be returned to its starting position.

The foregoing objects, advantages, features and results of the present invention, together with various other objects, advantages, features and results which will be evident to those skilled in the dental impression art in the light of this disclosure, may be achieved with the exemplary embodiment of the invention described in detail hereinafter and illustrated in the accompanying drawings.

BRIEF DESCRIPTION OF THE DRAWINGS

FIG. 6 is an enlarged sectional view taken as indicated by the arrowed line 6—6 of FIG. 2;

FIG. 7 is a fragmentary view duplicating a portion of FIG. 2 with some parts in different operating positions; and FIG. 8 is an enlarged cross-sectional view of the tip region of the instrument, showing the manner in which extruded impression material is attenuated and separated by the concentric air flow.

DETAILED DESCRIPTION OF THE INVENTION

Figure 1:
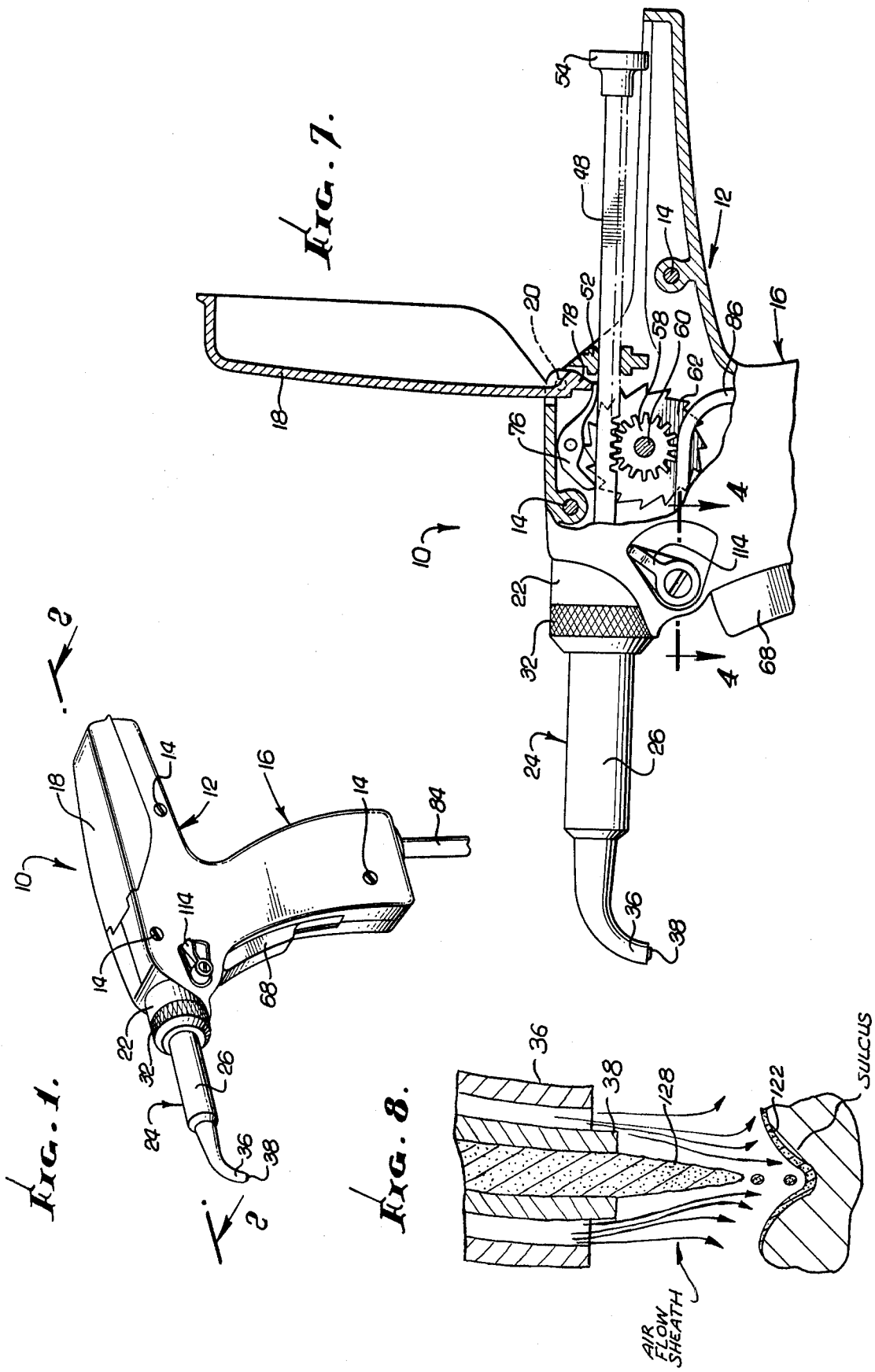
FIG. 1 is a perspective view of a gun-like instrument for making dental impressions which embodies the invention.

Referring to the drawing, the gun-like instrument of the invention is designated generally by the numeral 10 and includes a housing 12 shown as formed in two halves secured together by screws 14. The housing 12 includes a hand grip 16 much like a pistol grip.

The upper, rear portion of the housing 12 includes a cover 18 which is connected to the body of the housing by a transverse pivot 20. As will be apparent from a comparison of FIGS. 2 and 7, the cover 18 may be pivoted upwardly for access to the interior of the housing 12.

Clamped between the two halves of the housing 12, at the forward end of the housing and at the upper end of the hand grip 16, is a tubular member 22 which carries a nozzle assembly 24. This assembly includes an outer air nozzle 26 containing an inner nozzle 28 for impression material. The outer nozzle 26 is provided with an external annular flange 30 clamped against the forward end of the tubular member 22 by a knurled nut 32 threaded onto this tubular member.

The inner, impression nozzle 28 is spaced inwardly from the outer, air nozzle 26 to provide an air passage therebetween. The outer and inner nozzles 26 and 28 terminate in curved tips 36 and 38 which are also spaced apart to provide for compressed air flow therebetween. Preferably the spacing between the tips 36 and 38 is maintained by circumferentially spaced, longitudinally extending ribs 40, shown in FIG. 6.

As previously discussed, an important feature of the invention is that the inner tip 38 for the impression material projects beyond the outer tip 36 for the compressed air. With this construction, any possibility of plugging of the air nozzle 26 by the impression material is eliminated, which is an important feature.

The inner nozzle 28 includes a cylinder 42 which contains a supply of impression material 44. Disposed in the cylinder 42, and movable from the rearward end thereof toward the forward end thereof to expel impression material 44 through the inner tip 38, is a plunger 46 carried by a rack 48. The latter is coaxial with the plunger 46 and is supported by a guide 50 on the tubular member 22 and a guide 52 on the housing 12. The rack 48 is provided at its rearward end with a knob 54 for manual retraction of the plunger 46 upon opening of the cover 18.

As will be apparent, displacement of the plunger 46 toward the forward or outer end of the cylinder 42 will result in expelling the impression material 44 through the inner tip 38, which impression material may be caused to impinge on a tooth being worked on to form the desired impression. The plunger 46 is advanced in this manner by a pinion 58 meshed with the rack 48 and fixed on a transverse shaft 60 rotatably mounted in the housing 12, as best shown in FIG. 3. Also fixed on the shaft 60, adjacent the pinion 58, is a ratchet wheel 62. The ratchet wheel is rotated in the counterclockwise direction, as viewed in FIG. 2, to advance the plunger 46, by a pawl 64 pivotally mounted, at 66, on the upper end of a trigger 68, the pawl 64 being biased toward the ratchet wheel 62 by a spring 70. The lower end of the trigger 68 is pivotally connected, at 72, to the hand grip 16. The trigger 68 projects forwardly of the hand grip 16 so that it can be pivoted rearwardly readily by the operator's fingers when the operator is grasping the hand grip 16. The trigger 68 is biased forwardly by a spring 74 within the hand grip 16.

As will be apparent, squeezing the trigger 68 repeatedly causes the pawl 64 to rotate the ratchet wheel 62 and the pinion 58 incrementally. Consequently, the rack 48 and the plunger 46 are advanced in step-by-step fashion to expel the impression material 44 from the inner tip 38 incrementally. As previously explained, contemporaneous air blasts from the outer tip 36 cause the impression material to impinge on the tooth being worked on.

The housing 12 carries another pawl 76 which engages the ratchet wheel 62, opposite the pawl 64, to prevent reversed movement of the plunger 46 during forward pivoting of the trigger 68. The cover 18 carries a cam 78 which, as best shown in FIG. 7, engages the pawl 76, upon opening of the cover, to disengage the pawl 76 from the ratchet wheel 62. This permits manual retraction of the plunger 46 whenever a fresh charge of impression material 44 is required.

Figure 4:
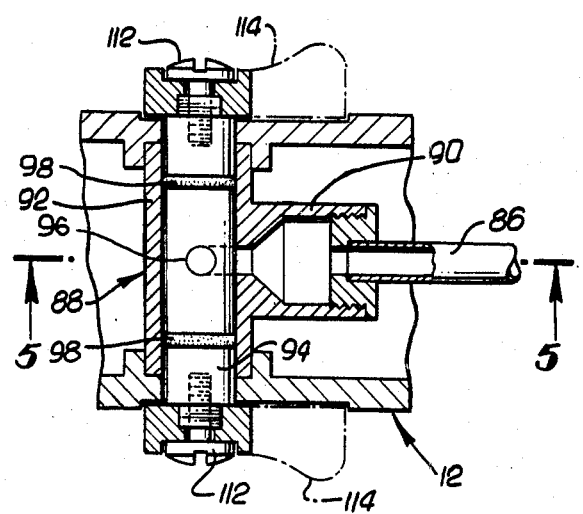
FIG. 4 is an enlarged, fragmentary sectional view taken as indicated by the arrowed line 4—4 of FIG. 7.
Figure 5:
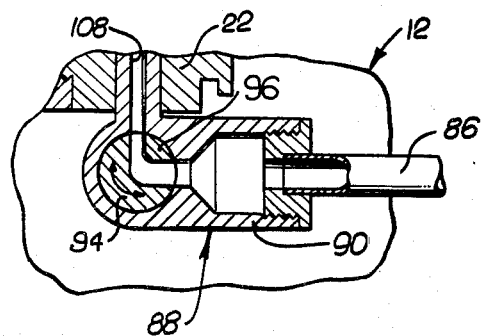
FIG. 5 is a sectional view taken as indicated by the arrowed line 5—5 of FIG. 4.

Turning now to a consideration of how compressed air is delivered to the outer nozzle 26, the butt of the hand grip 16 is provided with a fitting 82 to which a compressed air line 84 may be connected. The line 84 is connected to the usual compressed air source provided in a dentist's office. A tube 86 within the hand grip 16 leads to a T-shaped valve body 88, FIG. 4, mounted in the housing 12 adjacent the upper end of the trigger 68. The T-shaped body 88 includes a leg portion 90 and a crossbar portion 92 extending transversely of the hand grip 16 adjacent the tubular member 22.

Within the leg portion 90 of the valve body 88 is a rotary valve 94 having an interior conduit 96 which in the open position as shown provides a flow path between the inlet tube 86 and an outlet conduit 108. The rotary valve 94 is sealed by O-rings 98.

Figure 2:
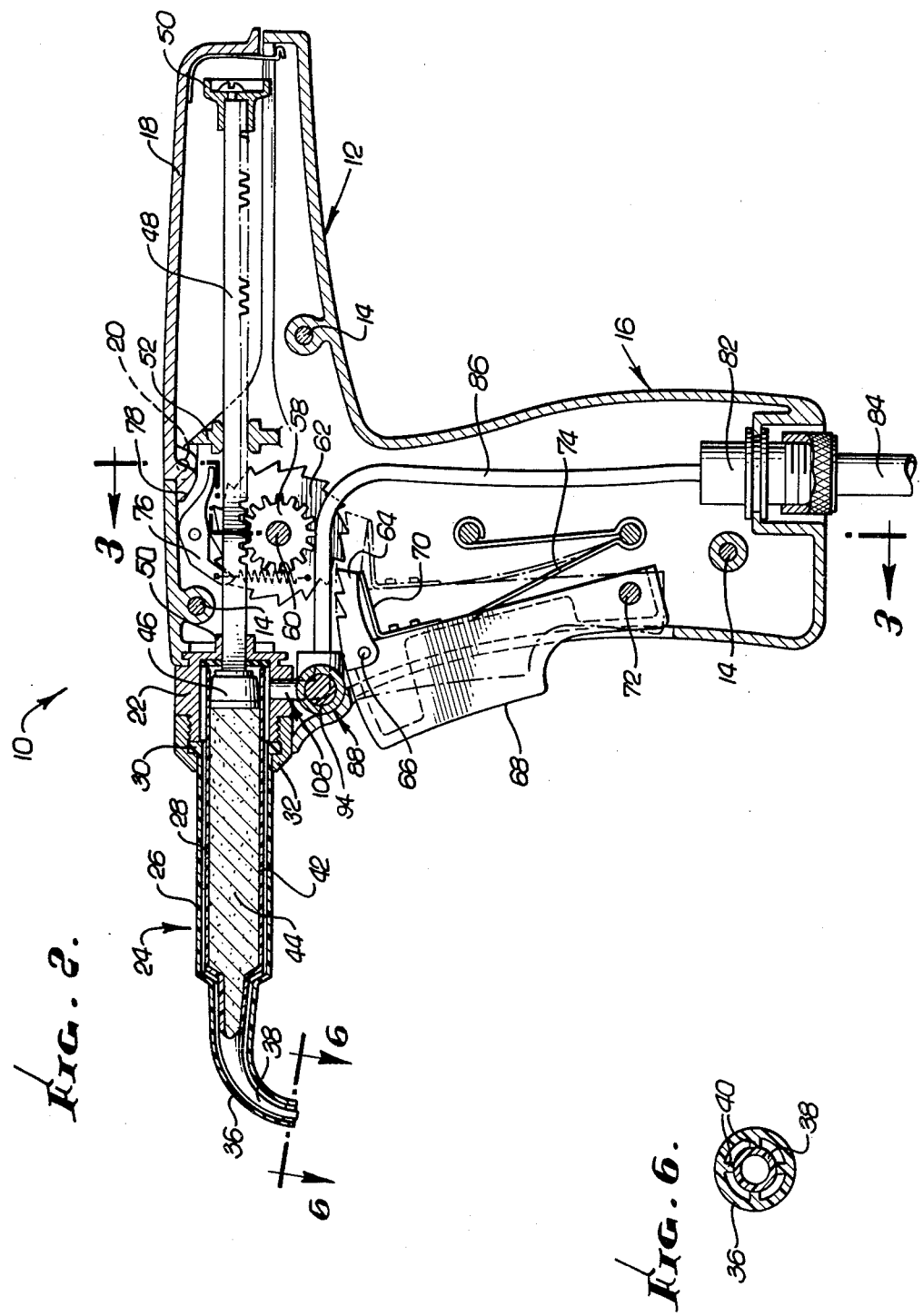
FIG. 2 is an enlarged sectional view taken as indicated by the arrowed line 2—2 of FIG. 1.
Figure 3:
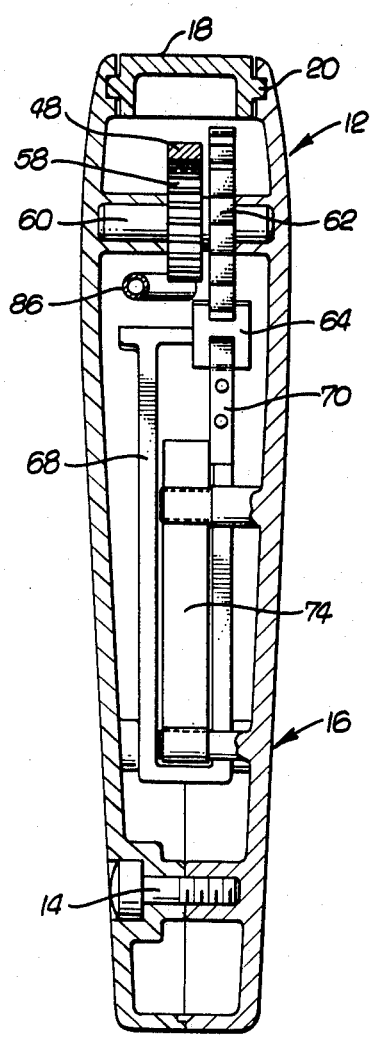
FIG. 3 is a transverse sectional view taken as indicated by the arrowed line 3—3 of FIG. 2.

As will be apparent, by rotating the valve 94 90°, compressed air is directed through a passage 108, FIG. 2, into the space between the inner, impression nozzle 28 and the outer, air nozzle 26 for discharge through the outer tip 36 of the nozzle assembly 24. As previously indicated, such compressed air may either be used to clean the tooth area being worked on, or to cause the impression material 44 to impinge on such area in building up the desired impression.

Considering the manner in which the valve 94 is opened to produce the desired air blast, or series of air blasts, the ends of the valve 94 are exposed on opposite sides of the housing 12 and have connected thereto, as by screws 112, thumb operable actuators 114 which are located on opposite sides of the housing 12 adjacent the upper end of the trigger 68.

With the foregoing construction, compressed air and impression material may be discharged selectively with one hand, using the fingers on the trigger 68 for the impression material and the thumb on one of the actuators 114 for the compressed air. Also, since there are two of the actuators 114 on opposite sides of the housing 12, the instrument may readily be operated by either a left-handed or a right-handed operator, which is an important feature.

The impression instrument may be used with a great majority of commercial available impression materials, such as those based on silicones, polyethers, polysulfides, vinylpolysiloxides and rubber base materials. Most of these materials have some adherent properties sufficient to form a thin film that is not carried away by subsequent air blasts. Some of the polyethers and silicones, on the other hand, have an excessively slippery characteristic and do not permit the instrument to be used to full advantage. The material is mixed together with a suitable catalyst just prior to application, and usually has a cure time of approximately four minutes. After mixing, therefore, a part of the material is placed in the receiving cylinder 42 in the impression instrument, and the remainder is used to fill a small form, called a tray, which is to be used in the final step of taking the impression.

In the present impression instrument a concentric sheath of air flowing at a substantial rate can be concentrated on the target area to provide immediate and concurrent drying. The flow rate is sufficiently high, with a source pressure of 30 psi typically being used, for the flow through the small outer nozzle (less than one-quarter inch in inner diameter) to force out excess seepage and dries off trace amounts of seepage. Because the inner tip 38 protrudes beyond the outer air tip 36, extrudate which moves past the end of the inner tip 38 is acted upon on all sides by the air flow sheath directed down into the concavity, when air flow is used. As best seen in FIG. 8, the rubbery and somewhat elastic characteristic of the impression material prevents the extrudate from separating from the extruded mass directly at the tip 38 of the inner nozzle. Instead, a length or column 120 of extrudate, typically one-quarter to three-eighths inches long, is formed that converges or is attenuated in the direction of air flow into a point. This point may be touched directly upon the target area to deposit a moderate mass of material, whether air is flowing or not. If more impression material is fed out, small globules of impression material separate off the protruding end of the extruded column 120 and move with the air flow to impinge on the dried target area. The small globules or deposited mass adhere where the target area is dry, but if it is not, the globules are displaced to one side or the other until the area is dried, at which point adherence begins. The accumulation of material is, very importantly, not a successive thickening or layering, which does not insure freedom from voids. Instead, when the material adheres the action of the air flow spreads it out into a thin film, as seen at 122 in FIG. 8. This film penetrates into and conforms to the interior of the concavity along the sulcus, as well as conforming to other concavities and convexities on the tooth. The dentist therefore can quickly move around the entire tooth, using various combinations of air flow and impression material feed control. The air flow can be used intermittently or continuously for drying purposes and the impression material can be deposited directly or advanced incrementally as needed for deposit. When the impression material has been formed into the desired band of deposited film about the gum line and the casting margin and onto and into the intricacies of the prepared tooth, for one or a number of teeth, the impression instrument need no longer be used. At this point the conventional tray that was previously filled with the remainder of the impression material is placed in position over the teeth and pressed down, urging impression material around the entire tooth. With the margins and concavities completely covered with a film of impression material, the application of the tray insures complete filling, because seepage is no longer a problem and because the added impression material readily adheres to that previously laid down. When the impression material is fully cured after a few minutes, it is removed for inspection and is thereupon ready for a dental technician.

Impressions made in this fashion substantially eliminate the need for subsequent tailoring of dies made from the impression, or extrapolation or interpolation of the margin lines. The impression that is taken is clear and undistorted, and free of voids and bubbles when the instrument is properly used, whether the dentist is able to observe the integrity of the film as it is being laid down, or not.

The tips can be reused if desired, but are of low cost molded plastic construction and typically are disposed of after one use or a limited continuous period of use. The detachable nozzle assembly can readily be rotated within the tightening ring on the housing, so that the curved tip points in any direction desired for depositing impression material on upper or lower teeth, while the handle remains in a convenient operative position. The convenience of operation and accessibility with this mechanism of all regions within the mouth of a patient enable the impression to be taken more rapidly, as well as more efficiently, than heretofore.

Although an exemplary embodiment of the invention has been disclosed for illustrative purposes, it will be understood that various changes, modifications and substitutions may be incorporated in such embodiment without departing from the invention as hereinafter claimed.

What is claimed is:

1. A dental impression instrument for providing an adherent thin film deposit within concave and convex target regions, in particular at the gum line, that are subject to seepage of blood and saliva when making an impression, the instrument comprising:
   first nozzle means providing a concentrated hollow cylindrical air flow of sufficient volumetric flow rate to dry the target area; and
   second nozzle means disposed within the first nozzle means and providing a cylindrical extrusion of chemically curing impression material within the air flow, the extrudate being attenuated by the air flow along the direction of flow to form a protrusion which may be deposited on a target area directly, or separate into globules impinging and spreading on the target area under the force of the air flow, such that the impression material is directed into a dry target area and is forced by the air flow to conform as an adhering thin film to the interior and exterior configuration of the target areas.

2. A dental impression instrument as set forth in claim 1 above, wherein the first nozzle means has a tip diameter of less than approximately one-quarter inch, and wherein said second nozzle means extends beyond said first nozzle means, each of said nozzle means having a tip region that is concentric with a central axis.

3. The impression instrument as set forth in claim 2 above, including in addition handle means coupled to said first and second nozzle means, said handle means including control means for one hand control of the air flow and impression material flow.

4. The impression instrument as set forth in claim 3 above, wherein said handle means includes means for control of the air flow with either hand.

5. The impression instrument as set forth in claim 3 above, wherein said control means for controlling impression material flow comprises means for incrementally advancing the impression material through the second nozzle means.

6. The impression instrument as set forth in claim 5 above, wherein the impression material is of the type which cures in an interval of the order of several minutes, has a viscous rubbery characteristic while curing, and is elastomeric when cured.

7. A dental impression instrument for one hand application of impression material, comprising:
   an impression gun having a handle and a body, the body lying along a first axis;
   a nozzle assembly detachably coupled to the body along the first axis and including a tip portion curved away from the first axis, the nozzle assembly including, at the tip region, an outer nozzle of less than approximately one-quarter inch in inner diameter, and an inner nozzle substantially concentric therewith;
   said gun further including means providing a controllable air flow of substantial flow rate through the first nozzle, further including control means on the gun accessible to at least one finger of the operator thereof; and
   means disposed within said gun for controllably extruding impression material through the inner nozzle, said means including control means accessible to at least one finger of the operator for extruding the impression material into the surrounding air flow;
   the air flow rate and impression material velocity being selected such that the air flow attenuates the extrudate into a protruding segment which may be directly deposited or alternatively may be separated off under the air flow globules which impinge and spread within a target region while the air flow concurrently keeps the target region dry.

8. The invention as set forth in claim 7 above, wherein the inner nozzle protrudes outside the outer nozzle.

9. The invention as set forth in claim 8 above, wherein said means for advancing the extrudate comprises finger operable means for incrementally extruding the impression material from the inner nozzle.

10. The invention as set forth in claim 9 above, wherein said means for providing a controllable air flow includes control lever means mounted on at least one side of the gun.

11. The invention as set forth in claim 10 above, wherein said nozzle assembly is rotatably positionable about the first axis on said body, and the nozzle tips extend at least partially transversely to the first axis, such that the flow of air and impression material may be directed toward upper or lower teeth with the handle in a convenient operative position.

12. A hand held device for feeding a solid pliable impression material into a tooth cavity to make a dental impression utilizing a compressed gas, comprising;
   an impression material nozzle having a curved tip and an orifice diameter in the range of approximately one-eighth inch;
   a source of solid, pliable rubbery impression material in a chemically curing state and extrudable under pressure;
   manually operable means in communication with the nozzle for feeding the impression material through the nozzle;
   an air nozzle having a tip region concentric with the impression material nozzle but terminating short of the end thereof, the air nozzle providing a concentric air flow sheath about the impression material column with sufficient velocity to impel globules of impression material onto a target region that is concurrently dried by the air flow; and
   manually controllable means governing the flow of compressed air through the air nozzle.

13. In an instrument for making dental impressions, the combination of:
   (a) a gun including a hand grip and having an air nozzle and a second nozzle for impression material adjacent said air nozzle;
   (b) a finger operable trigger pivotally mounted on said gun adjacent and forwardly of said hand grip;
   (c) means controlled by said trigger for discharging impression material from said second nozzle;
   (d) valve means for discharging air from said air nozzle;
   (e) a first thumb operable valve actuator for said valve means mounted on one side of said gun adjacent the upper end of said trigger; and
   (f) a second thumb operable valve actuator for said valve means mounted on the opposite side of said gun from said first thumb operable valve actuator, whereby said instrument may be operated by either a left-handed or a right-handed operator.

14. A method for use in making dental impressions, including the steps of selectively centrally discharging a dental impression material toward a target area in which an impression is to be taken, selectively flowing an annular stream of air around the region of discharge of the impression material to dry the target area and spread the discharged material on the tooth into intimate contact with the contour of the target area, successively covering all areas for which the impression is to be taken, allowing the impression material to set, and removing the impression material to provide the dental impression.

15. The method of making dental impressions comprising the steps of selectively advancing a column of viscous rubbery impression material in a chemically curing state along a first axis, selectively flowing a cylindrical sheath of air about the viscous material to form a converging protrusion of impression material, drying target areas with the air flow, selectively directly depositing impression material on target areas or separating off globules under the force of air flow to cause impingement on the target areas, spreading deposited material into a thin film with the air flow to form an adherent layer that conforms to the concavities and convexities on the target areas, continuing the above steps to cover at least all the margins and concavities in the chosen overall area for which an impression is desired, placing a tray substantially filled with impression material over the chosen area to unite with the previously deposited material, allowing the material to cure in place, and removing the impression material to provide the dental impression.

16. In a nozzle assembly for an instrument for making dental impressions, the combination of:
   (a) an outer, air nozzle;
   (b) an inner nozzle for impression material located concentrically within said outer nozzle;
   (c) spacing means between said inner and outer nozzles for spacing said inner nozzle inwardly from said outer nozzle with said inner nozzle located concentrically within said outer nozzle;
   (d) the space between said outer nozzle and said inner nozzle constituting a substantially annular air passage around said inner nozzle; and
   (e) said inner and outer nozzles terminating at outer ends thereof in curved portions which provide said nozzle assembly with a curved tip for discharging air and dental impression material transversely of said nozzle assembly.

17. A nozzle assembly as defined in claim 16 wherein said inner nozzle terminates at its outer end in an endwise-facing open end located beyond said outer end of said outer nozzle.

18. A nozzle assembly according to claim 17 wherein said inner nozzle has a cylindrical inner end portion extending longitudinally beyond the inner end of said outer nozzle a substantial distance to receive a piston for expelling dental impression material from said inner nozzle.

19. A nozzle assembly as defined in claim 18 wherein said spacing means comprises circumferentially spaced elements dividing said substantially annular air passage into circumferentially spaced segments.

20. In a nozzle assembly for use with a dental impression instrument having means for mounting said nozzle assembly thereon and having a cylindrical piston for expelling dental impression material from said nozzle assembly, the combination of:
   (a) an outer, air nozzle having inner and outer ends;
   (b) an inner nozzle for impression material located concentrically within said outer nozzle and having inner and outer ends;
   (c) said inner end of said inner nozzle being cylindrical and projecting beyond said inner end of said outer nozzle and receiving said piston of said instrument when said nozzle assembly is mounted on said instrument;
   (d) spacing means between said inner and outer nozzles for spacing said inner nozzle inwardly from said outer nozzle with said inner nozzle located concentrically within said outer nozzle;
   (e) the space between said outer nozzle and said inner nozzle constituting a substantially annular air passage around said inner nozzle; and
   (f) said inner and outer nozzles terminating at their outer ends in curved portions which provide said nozzle assembly with a curved tip for discharging air and dental impression material at least partially transversely of said nozzle assembly.

* * * * *